(12) United States Patent
Venczel

(10) Patent No.: US 9,970,904 B2
(45) Date of Patent: *May 15, 2018

(54) OBLIQUE FLAW DETECTION USING ULTRASONIC TRANSDUCERS

(71) Applicant: Magnetic Analysis Corporation, Mount Vernon, NY (US)

(72) Inventor: John Venczel, South Salem, NY (US)

(73) Assignee: Magnetic Analysis Corporation, Mount Vernon, NY (US)

( * ) Notice: Subject to any disclaimer, the term of this patent is extended or adjusted under 35 U.S.C. 154(b) by 200 days.

This patent is subject to a terminal disclaimer.

(21) Appl. No.: 14/679,519

(22) Filed: Apr. 6, 2015

(65) Prior Publication Data

US 2015/0212049 A1  Jul. 30, 2015

Related U.S. Application Data

(63) Continuation of application No. 13/845,918, filed on Mar. 18, 2013, now Pat. No. 8,997,574, which is a
(Continued)

(51) Int. Cl.
*G01N 29/04* (2006.01)

(52) U.S. Cl.
CPC ........... *G01N 29/04* (2013.01); *G01N 29/043* (2013.01); *G01N 2291/044* (2013.01);
(Continued)

(58) Field of Classification Search
CPC ................. G01N 29/043; G01N 29/04; G01N 2291/0422; G01N 2291/044;
(Continued)

(56) References Cited

U.S. PATENT DOCUMENTS 3,183,709 A    3/1965   Rankin et al.
3,218,845 A   11/1965   Joy
(Continued)

FOREIGN PATENT DOCUMENTS

DE    40 27 161 A1    3/1992
DE    44 10 580 A1   10/1994

OTHER PUBLICATIONS

Schmeisser, M. et al., "A New Method for the Detection of Obliquely Oriented Defects," Magnetic Analysis Corp., Feb. 19, 1991.

*Primary Examiner* — J M Saint Surin
(74) *Attorney, Agent, or Firm* — Haley Guiliano LLP

(57) ABSTRACT

Ultrasonic transducers and methods for detecting oblique flaws in cylindrically-shaped objects using pulse-echo testing are provided. By mounting one or more transducers on a rotary tester for testing manufactured objects such as tubes and bars, offsetting each transducer horizontally from its position if it were to emit a beam that is perpendicular to the object's outer surface, and actuating the transducer so as to emit an angled beam, oblique surface flaws and internal flaws may be reliably detected without reducing inspection speed, significantly adding to transducer cross-talk, or requiring significant additional hardware or processing.

20 Claims, 7 Drawing Sheets

Related U.S. Application Data continuation of application No. 12/823,600, filed on Jun. 25, 2010, now Pat. No. 8,397,575, which is a continuation of application No. 11/891,132, filed on Aug. 8, 2007, now Pat. No. 7,757,559.

(60) Provisional application No. 60/931,801, filed on May 25, 2007.

(52) U.S. Cl.
CPC ........... *G01N 2291/0422* (2013.01); *G01N 2291/056* (2013.01); *G01N 2291/101* (2013.01); *G01N 2291/2634* (2013.01)

(58) Field of Classification Search
CPC ..... G01N 2291/101; G01N 2291/2634; G01N 2291/056
USPC .......................................................... 73/632
See application file for complete search history.

(56) References Cited

U.S. PATENT DOCUMENTS

| | | | |
|---|---|---|---|
| 3,289,468 A | 12/1966 | Van der Veer et al. | |
| 3,379,051 A | 4/1968 | Zeutschel et al. | |
| 3,693,415 A | 9/1972 | Whittington | |
| 3,924,453 A * | 12/1975 | Clark | G01N 29/043 73/622 |
| 4,022,055 A | 5/1977 | Flournoy et al. | |
| 4,070,905 A | 1/1978 | Kossoff | |
| 4,088,029 A | 5/1978 | Yamamoto et al. | |
| 4,195,530 A | 4/1980 | Ross et al. | |
| 4,254,661 A | 3/1981 | Kossoff et al. | |
| 4,289,033 A | 9/1981 | Prause et al. | |
| 4,319,490 A | 3/1982 | Hartmann, Jr. | |
| RE30,926 E | 5/1982 | Ross et al. | |
| 4,352,294 A | 10/1982 | Perodjon | |
| 4,353,258 A | 10/1982 | Hunter | |
| 4,399,703 A | 8/1983 | Matzuk | |
| 4,401,910 A | 8/1983 | Beerman | |
| 4,478,083 A | 10/1984 | Hassler et al. | |
| 4,676,106 A | 6/1987 | Nagai et al. | |
| 4,815,043 A | 3/1989 | Shirasaka | |
| 4,987,563 A | 1/1991 | Gilmour | |
| 5,062,300 A | 11/1991 | Vallee | |
| 5,123,415 A | 6/1992 | Daigle | |
| 5,165,280 A | 11/1992 | Sternberg et al. | |
| 5,165,414 A | 11/1992 | Larson, III | |
| 5,272,908 A | 12/1993 | Soss | |
| 5,297,553 A | 3/1994 | Sliwa, Jr. et al. | |
| 5,421,200 A | 6/1995 | Casarcia et al. | |
| 5,431,054 A | 7/1995 | Reeves et al. | |
| 5,460,046 A | 10/1995 | Maltby et al. | |
| 5,493,541 A | 2/1996 | Snyder | |
| 5,553,500 A | 9/1996 | Grahn et al. | |
| 5,779,639 A | 7/1998 | Yeung | |
| 5,932,807 A | 8/1999 | Mallart | |
| 5,963,882 A | 10/1999 | Viertl et al. | |
| 6,310,426 B1 | 10/2001 | Birchak et al. | |
| 6,725,721 B2 | 4/2004 | Venczel | |
| 6,745,136 B2 | 6/2004 | Lam et al. | |
| 6,813,950 B2 | 11/2004 | Glascock et al. | |
| 6,945,113 B2 | 9/2005 | Siverling et al. | |
| 7,757,559 B2 | 7/2010 | Venczel | |
| 7,975,549 B2 | 7/2011 | Fetzer et al. | |
| 8,397,575 B2 * | 3/2013 | Venczel | G01N 29/043 73/622 |
| 8,997,574 B2 * | 4/2015 | Venczel | G01N 29/043 73/622 |
| 2009/0320601 A1 | 12/2009 | Kleinert | |

* cited by examiner

OBLIQUE FLAW DETECTION USING ULTRASONIC TRANSDUCERS

CROSS REFERENCE TO RELATED APPLICATION

This application is a continuation of U.S. application Ser. No. 13/845,918 filed Mar. 18, 2013, which is a continuation of U.S. application Ser. No. 12/823,600 filed Jun. 25, 2010, now U.S. Pat. No. 8,397,575, which is a continuation of U.S. application Ser. No. 11/891,132 filed Aug. 8, 2007, now U.S. Pat. No. 7,757,559, and which claims the benefit of U.S. Provisional Application No. 60/931,801, filed May 25, 2007, all of which are incorporated by reference herein in their entirety.

FIELD OF THE INVENTION

The present application relates to an invention for inspecting tubes, bars, pipes, and other objects using ultrasonic transducers. More particularly, the invention is concerned with performing pulse-echo testing to detect oblique flaws in such objects using offset and angled ultrasonic transducers.

BACKGROUND OF THE INVENTION

Ultrasonic inspection is commonly used to detect flaws, such as surface flaws (e.g., cracks), internal flaws (e.g., voids or inclusions of foreign material), and other defects. It is also used to measure wall thickness in tubes and pipes as well as bar diameters. In what is known as the pulse-echo method for testing, the same transducer serves both as a transmitter and a receiver of ultrasonic beams or waves used to detect such flaws and take such measurements.

When testing using the pulse-echo method, a transducer produces a pressure wave referred to as an ultrasonic pulse in response to an electrical pulse. The pressure wave travels through a coupling medium between the transducer and the tested object. Once the ultrasonic pulse reaches an interface between the coupling medium and the tested object, a portion of the pulse enters the object whereas another portion is reflected back to the transducer (i.e., a partial reflection and transmission occur). The initially reflected pulse is known as a frontwall echo. The portion of the pulse that enters the object continues until the back wall, where another partial reflection and transmission occur. This partial reflection is known as the backwall echo. If there is an internal flaw in the tested object for instance, a portion of the ultrasonic pulse is also reflected back to the transducer at the flaw. The flaw can be located knowing the elapsed time between the different reflections.

For automatic flaw testing, a gate is placed between the frontwall and backwall echoes. Any pulse within the gate area may be peak detected, producing an analog output that can be recorded and that represents a flaw in the tested object. In addition, thickness measurements are made possible knowing the time difference between the backwall and frontwall echo pulses as well as the velocity of the ultrasonic wave as it travels through the medium of the tested object.

The most widely used pulse-echo process for non-destructive testing of objects such as tubes and bars is performed by using ultrasonic rotary testers. Ultrasonic transducers are mounted on a rotary testing unit of such testers, while the tube or bar to be tested is moved freely through the tester. Rotating the transducers in the tester around the tube as opposed to rotating the tube as it is moved through the tester eliminates the need for heavy machinery and high power in the case of testing large and long tubes and bars. The space between the object and transducers is generally filled with water in order to provide coupling for the ultrasonic beam. The electrical signals from the ultrasonic inspection instrument are connected to the rotating transducers by rotary capacitors. In order to detect various kinds of surface and internal flaws and to provide thickness measures, several transducers may be mounted on the tester, each being oriented to perform a specific function.

For instance, in a longitudinal wave inspection arrangement, a transducer is typically oriented so that the ultrasonic beam is perpendicular to the surface of the tested object. In such a case, the angle of incidence is 90 degrees. The resulting longitudinal waves travel along a path that is aligned with the radial axis of the tested object and are therefore suitable for taking thickness or diameter measurements and detecting certain inner flaws.

When the angle of incidence is not 90 degrees, refraction occurs and the ultrasonic beam splits into two parts in a solid material: a longitudinal wave beam and a shear wave beam. In longitudinal waves, particle motion is parallel to the direction of wave propagation. In shear waves, however, particle motion is perpendicular to the direction of wave propagation. The refraction angle of the longitudinal wave beam is greater than that of the shear wave beam. Accordingly, when the angle of incidence exceeds a particular value, the longitudinal wave beam ceases to exist and only the shear wave beam remains. This angle is called the first critical angle. Shear waved can be used to detect both surface and internal flaws.

For flaw detection of surface and internal flaws in tubes and bars, shear wave testing is commonly used. FIG. 1 illustrates a setup for performing one type of such a test on a tube. To improve the detectability of irregularly shaped flaws, shear waves are generated in both clockwise and counter-clockwise directions simultaneously using two offset transducers 110. Each incident beam 120 of transducers 110 is maintained within the same plane of a cross section that is perpendicular to longitudinal axis 150 of tube 130, while offsetting it from radial axis 180. The magnitude of offset is proportional to the diameter of the tube.

Under the setup of FIG. 1, beams 122 and 144 travel generally clockwise and counter-clockwise, respectively, in the plane of cross section, bouncing between the outer and inner surfaces of tube 130 until a flaw is detected and beam 120 is partially reflected back to transducer 110. As shown in FIG. 1, the beam traveling clockwise, beam 122, is reflected back from an inner diameter crack 160, while the beam traveling counter-clockwise, beam 144, is reflected back from an outer diameter crack 170.

Such an arrangement, whereby the transducer is offset while its beam remains within the same plane of the tube's cross section, is suitable for detecting longitudinal flaws, i.e., flaws that are generally parallel to the tested object's longitudinal axis. However, in order to detect transverse flaws (i.e., flaws that are generally perpendicular to the tube's longitudinal axis), another arrangement is more appropriate. More specifically, the transducer is preferably angled in a plane containing the tube's longitudinal axis without offsetting the transducer from its position when it performs longitudinal wave testing. FIG. 2 illustrates a setup for performing such a test on a tube.

In FIG. 2, transducer 210 is angled in a plane containing longitudinal axis 150 and radial axis 180 of tube 130 without offsetting transducer 210 from its position when it performs longitudinal wave testing. Incident beam 120 of transducer 210 is maintained within the same plane of radial axis 180 and longitudinal axis 150 of tube 130 without creating the offset depicted in FIG. 1. Beam 222 of transducer 210 travels generally along the length of tube 130, in the plane containing radial axis 180 and longitudinal axis 150, bouncing between the outer and inner surfaces of tube 130 until a flaw is detected and beam 120 is partially reflected back to transducer 110. Beam 222 is partially reflected back from transverse crack 260 and beam 220 is partially reflected back to transducer 210. Transducer 210 can be oriented for forward-, or reverse-looking shear wave testing.

Referring to both FIGS. 1 and 2, tube 130 can be scanned if a set of transducers is rotated around longitudinal axis 150 while tube 130 is freely moved along longitudinal axis 150. To allow for thickness measurement and to ensure full flaw detection, several transducers are mounted in the rotary tester. Transducers can be oriented generally for longitudinal wave testing, while other transducers can be oriented for clockwise and counter-clockwise shear wave testing as shown in FIG. 1 and yet other transducers can be oriented for forward-, and reverse-looking shear wave testing as shown in FIG. 2. In this manner, five channels are required so that each transducer can be individually driven to achieve full-volume testing that measures thickness and detects internal flaws as well as surface flaws.

The above discussion outlines how shear waves can be used to detect internal or surface flaws. Offsetting a transducer without angling it, as shown in FIG. 1, can be used to detect longitudinal flaws, but will very likely miss transverse flaws. On the other hand, angling a transducer without offsetting it, as shown in FIG. 2, can be used to detect transverse flaws but will very likely miss longitudinal flaws. The orientations of longitudinal and transverse flaws may vary +/−5 degrees and still be detected by either offsetting or angling the transducer. However, such shear wave testing will likely miss naturally occurring flaws which are more commonly oriented at some angle such that they are neither longitudinal nor transverse given that the larger portions of the beam will likely not be reflected back to the transducer when bouncing off these flaws. Such flaws may be referred to as oblique flaws.

In view of the foregoing, it would be desirable to provide an ultrasonic transducer arrangement for detecting oblique flaws using pulse-echo testing.

SUMMARY OF THE INVENTION

It is therefore an object of the invention to provide an ultrasonic transducer arrangement for detecting oblique flaws using pulse-echo testing.

This and other objects may be achieved through systems and methods that utilize an angled ultrasonic transducer that may be mounted on a testing unit and offset from its position if it were to emit a beam perpendicular to the object's outer surface. More specifically, when testing a cylindrically-shaped object, the transducer may be positioned so that its axis is parallel to a plane that is defined by the longitudinal axis and a radial axis of the object. When the transducer is actuated, it emits an ultrasonic beam at an angle from the transducer axis onto the outer surface of the object. The plane defined by the emitted beam and the transducer axis may be parallel to the plane defined by the longitudinal and radial axes of the object.

As a result, this approach may produce shear waves that travel through the object along a spiral path that has two components: one component that is generally circular and that lies within the plane of the object's cross section, and one component that is generally along the length of object. The resulting direction of travel is at a desired angle, (e.g., a 45-degree angle) from each of the first and second components.

The magnitude of the offset may depend on the angle between the transducer axis and the emitted beam (i.e., the setting angle) and may be proportional to the diameter of the object. The setting angle may be determined based on a desired angle at which the emitted beam is designated to refract upon entering the object (e.g., a 45-degree refraction angle), and based on the ratio of the velocity of sound in a coupling medium to the velocity of sound in the object. When detecting flaws in steel tubes while immersing the transducer in water, the setting angle may be built into the transducer and chosen to be approximately 13.5 degrees.

The transducer may include a transducer element that is partially contained within a cylindrically-shaped housing having one end that is generally cut along a plane so as to emit a beam at the desired setting angle. The transducer element may include rods of piezoelectric ceramic material and a polymer material in which the rods are embedded.

One or more transducer of the type(s) described above may be mounted on an ultrasonic inspection system that includes a rotary testing unit configured to receive the object to be tested (such as a tube or a bar), and an actuator configured to actuate the transducer(s). Such transducers may be used for oblique flaw detection as well as transverse and longitudinal flaw detection, longitudinal wave testing, thickness measurements, etc.

BRIEF DESCRIPTION OF THE DRAWINGS

Further features of the invention, its nature and various advantages will be more apparent from the following detailed description of the preferred embodiments, taken in conjunction with the accompanying drawings, in which like reference characters refer to like parts throughout, and in which.

DETAILED DESCRIPTION OF THE INVENTION

Figure 1:
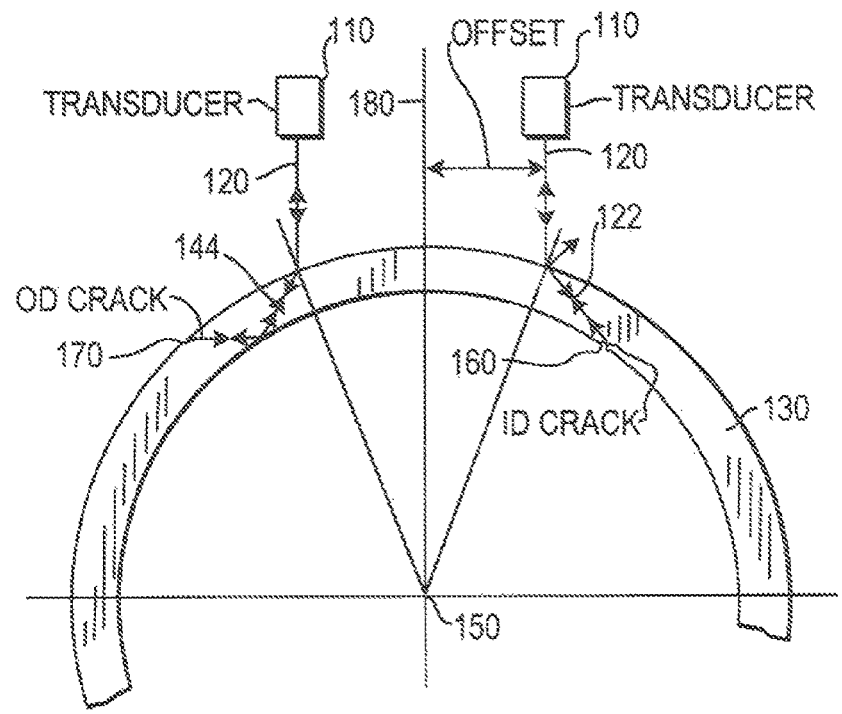
FIG. 1 is a cross-sectional view of a tube with two transducers in a conventional arrangement for performing shear wave testing for detecting longitudinal flaws.
Figure 2:
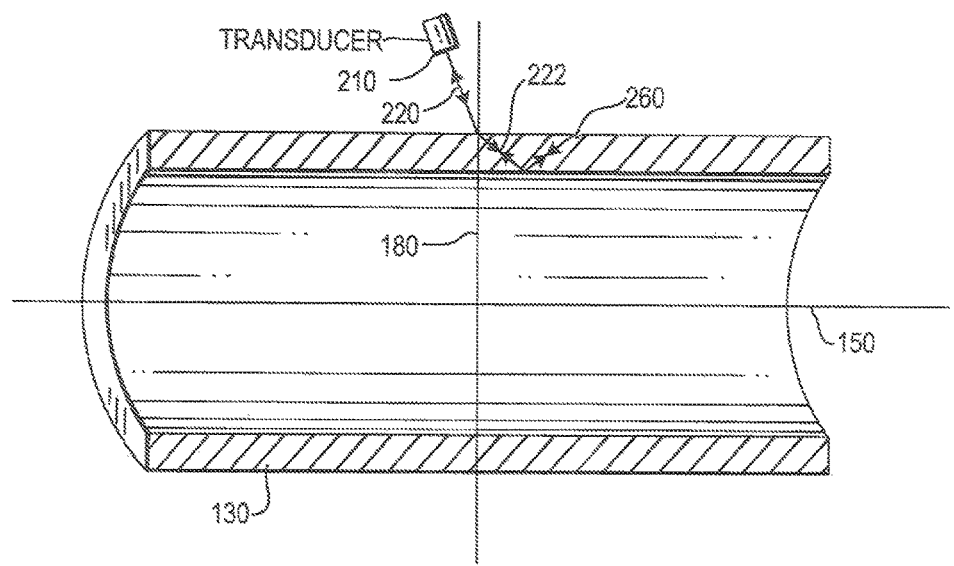
FIG. 2 is a cross-sectional view of a tube with a single transducer in a conventional arrangement for performing shear wave testing for detecting transverse flaws.

The present invention relates to systems and methods for inspecting tubes, bars, pipes, and other objects using ultrasonic transducers. More particularly, the invention relates to transducers that are used in pulse-echo testing to detect oblique internal or surface flaws using shear waves. As discussed above, simply offsetting a transducer without angling it, as shown in FIG. 1, can be used to detect longitudinal flaws, while angling a transducer without offsetting it, as shown in FIG. 2, can be used to detect transverse flaws.

In order to detect the more common, naturally occurring, oblique flaws that are neither transverse nor longitudinal, an approach that combines, yet modifies, both techniques using the same transducer may be provided in the present invention. As a result, this approach may produce shear waves that travel through the object being tested along a spiral path that has two components: one component that is generally circular and that lies within the plane of the object's cross section, and one component that is generally along the length of object. The resulting direction of travel is at an angle from each of the first and second components.

Figure 3:
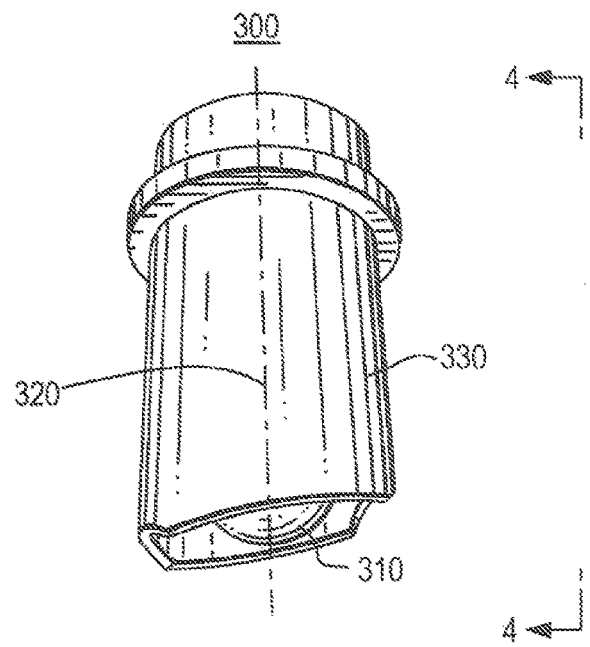
FIG. 3 is a perspective view of an illustrative transducer in accordance with certain embodiments of the present invention.
Figure 4:
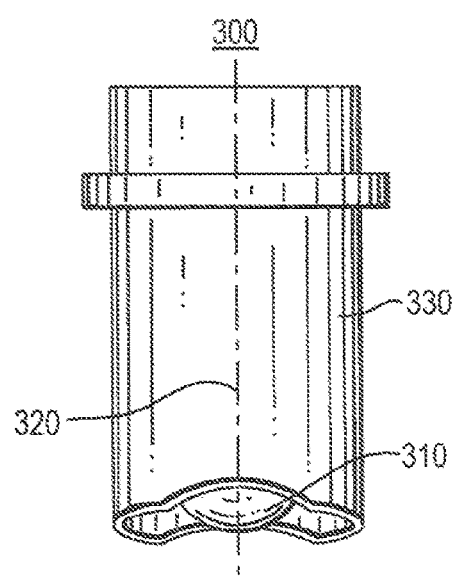
FIG. 4 is a top view of the illustrative transducer of FIG. 3, taken generally along the line 4-4, in accordance with certain embodiments of the present invention.

FIGS. 3 and 4 offer two views of an illustrative transducer 300 for use in the present invention. FIG. 4, is a view of transducer 300 taken generally along line 4-4 of FIG. 3. Transducer 300 may be manufactured so as produce an angled beam that is cylindrically focused. Cylindrically focused transducers provide the desired uniformity in terms of detection sensitivity in connection with shear wave testing.

Ultrasonic pulses may be emitted and received from the bottom surface of transducer 300. Transducer 300 may include transducer element 310 and housing 330. The bottom part of housing 330 may or may not cover the surface of transducer element 310, so long as ultrasonic pulses can travel back and forth from and to transducer element 310. Transducer 300 may be cylindrically shaped with a designated angle built into transducer housing 330. The designated angle (which may also be referred to as the setting angle) may be the angle between the beam emitted by transducer element 310 and axis 320 which corresponds to the axis of housing 330. Housing 330 may be generally cut along a plane that is not perpendicular to axis 320 in order to generate the shape that results in the beam being angled.

Housing 330 may be roughly 1.75 inches long and may have a diameter of about 1 inch. Transducer element 310 may be round and may have a diameter of about 0.6 inches. Such transducers are appropriate for testing bars and tubes with an outer diameter of approximately 2.5 inches. Best results may be achieved when the beams emitted by these transducers are focused at a point along the longitudinal axis of the tested tube or bar. Accordingly, the focal length of transducer element 310 may be 2.5 inches. Although several beams may emanate from transducer element 310, a single beam may be referred to as being emitted along a path that connects the center of element 310 with the point into which the constituent beams are focused.

It is understood that while transducer 300 is illustrated as a single-element transducer, a multi-element transducer arranged in a linear array or along multiple rows may alternatively be provided. It is also understood that the present invention may be used with bars and tubes of any suitable outer diameters.

Transducer element 310 may be made of any suitable material such as piezoelectric material. Transducer element 310 is preferably made of thin rods of piezoelectric ceramic elements embedded into a polymer material. The electrical and ultrasonic properties of transducer 300 may depend on the microstructure and the properties of the materials constituting transducer element 310. Transducer 300 may be connected to a coaxial cable (not shown) such that electric signals sent through the cable may drive transducer element 310. Similarly, echoes received by transducer element may be communicated through electric signals through the cable.

The previous discussion relating to FIGS. 3 and 4 describes one particular embodiment of transducer 300. However, the dimensions and properties of transducer 300 are not limited to the ones mentioned above and may be varied based on the dimensions and properties of the object to be tested or other considerations.

Figure 5:
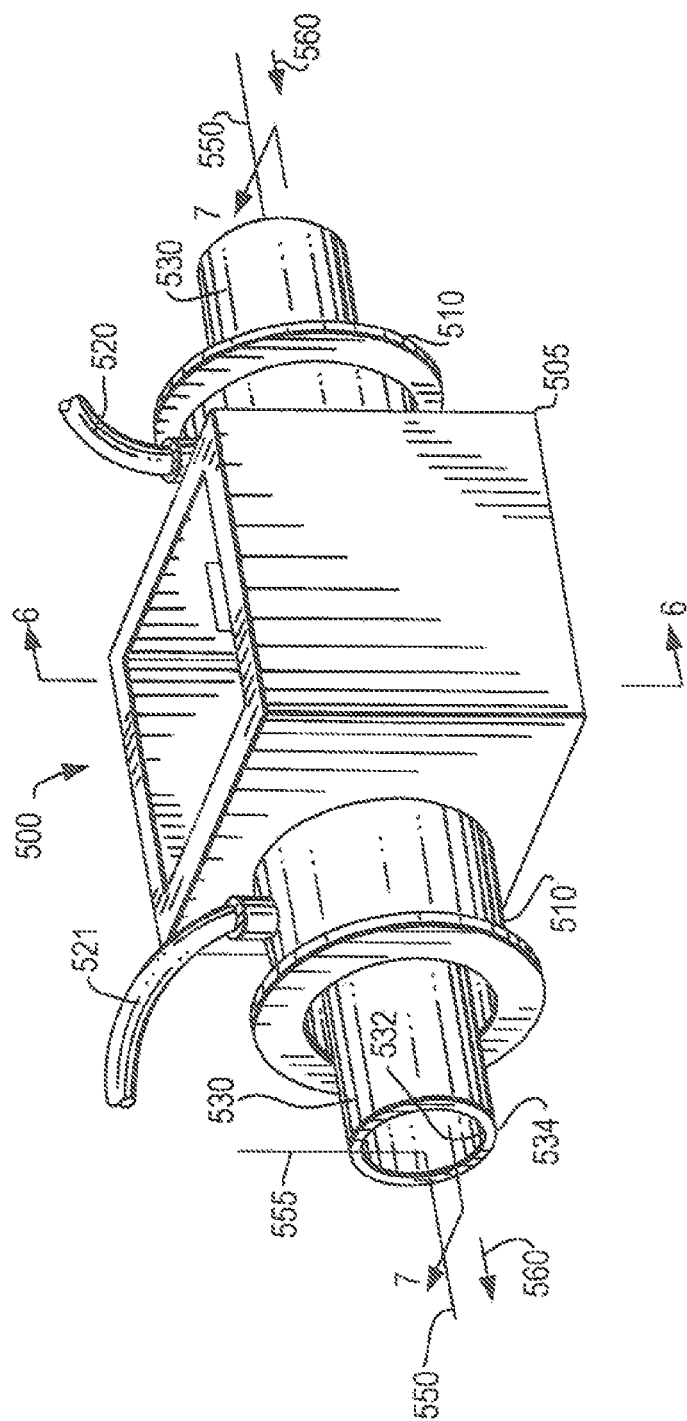
FIG. 5 is a perspective view of an illustrative rotary tester testing a tube in accordance with certain embodiments of the present invention.

FIG. 5 illustrates a tube 530 being tested by rotary tester 500. Tube 530 has longitudinal axis 550. The main body of tester 500 may be enclosed within a cubical frame 505, from which two outer shafts 510 may extend. Tube 530 may enter tester 500 from one of outer shafts 510 such that the center of tube 530 (i.e., longitudinal axis 550) passes through the centers of shafts 510 and tester 500. Tube 530 may also be allowed to move freely in direction 560 along the tube's longitudinal axis 550 without directly coming in contact with any part of tester 500. Tube 530 is shown to have inner surface 532 and outer surface 534. Tester 500 may include a testing unit (not shown in FIG. 5, but shown in FIGS. 6 and 7), which is enclosed within cubical frame 505. Hoses 520 and 521 can be used to deliver and cycle coupling medium to and through tester 500. The coupling medium (not shown in FIG. 5, but shown in FIGS. 6 and 7) may be any suitable medium in which ultrasonic waves may propagate freely. Water may be chosen as coupling medium mainly because it is inexpensive. As tube 530 is being tested, the coupling medium may be delivered through hose 520 at one of outer shafts 510, while the coupling medium may exit through hose 521 at the other outer shaft 510. As tube 530 is moved through tester 500, the coupling medium may be pumped and cycled through the testing unit in tester 500. Shafts 510 may include seals that may keep the water contained within the testing unit.

Figure 6:
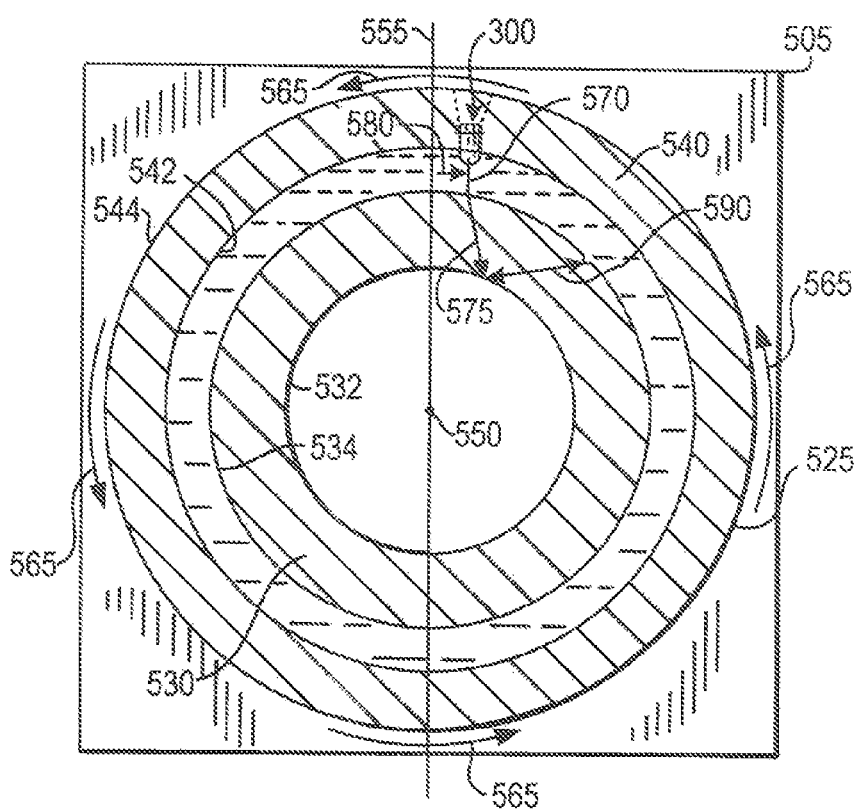
FIG. 6 is a cross-sectional view of the rotary tester and tube of FIG. 5, taken generally along the line 6-6, and showing the illustrative transducer of FIGS. 3-4 in accordance with certain embodiments of the present invention.

As previously mentioned, tube 530 may be rotated about axis 550 as it is being tested. However, as shown in FIG. 6, which is a cross-sectional view of rotary tester 500 and tube 530 taken generally along line 6-6 of FIG. 5, testing unit 540, which is enclosed within cubical frame 505, may be rotated about axis 550 in, for example, counter-clockwise direction 565. Coupling medium 525 remains in contact with both the outer surface 534 of tube 530 and the inner wall 542 of testing unit 540, therefore filling the space between tube 530 and testing unit 540 during testing. The rotational speed may be between 1800 and 4000 RPM, allowing a testing speed of up to 400 feet per minute.

In addition to longitudinal axis 550, which intersects the centers of both tube 530 and testing unit 540, there is radial axis 555, which is perpendicular to and intersects longitudinal axis 550, and which lies within the plane of FIG. 6. Transducer 300 may be mounted within testing unit 540 so as to test for oblique flaws. As such, transducer 300, which is angled, may be mounted within testing unit 540 and offset in direction 580 from its position if it were to emit a beam perpendicular to tube 530's outer surface 534, as shown in FIG. 6. As a result, the emitted ultrasonic beam 570 is not perpendicular to tube 530's outer surface 534.

Figure 7:
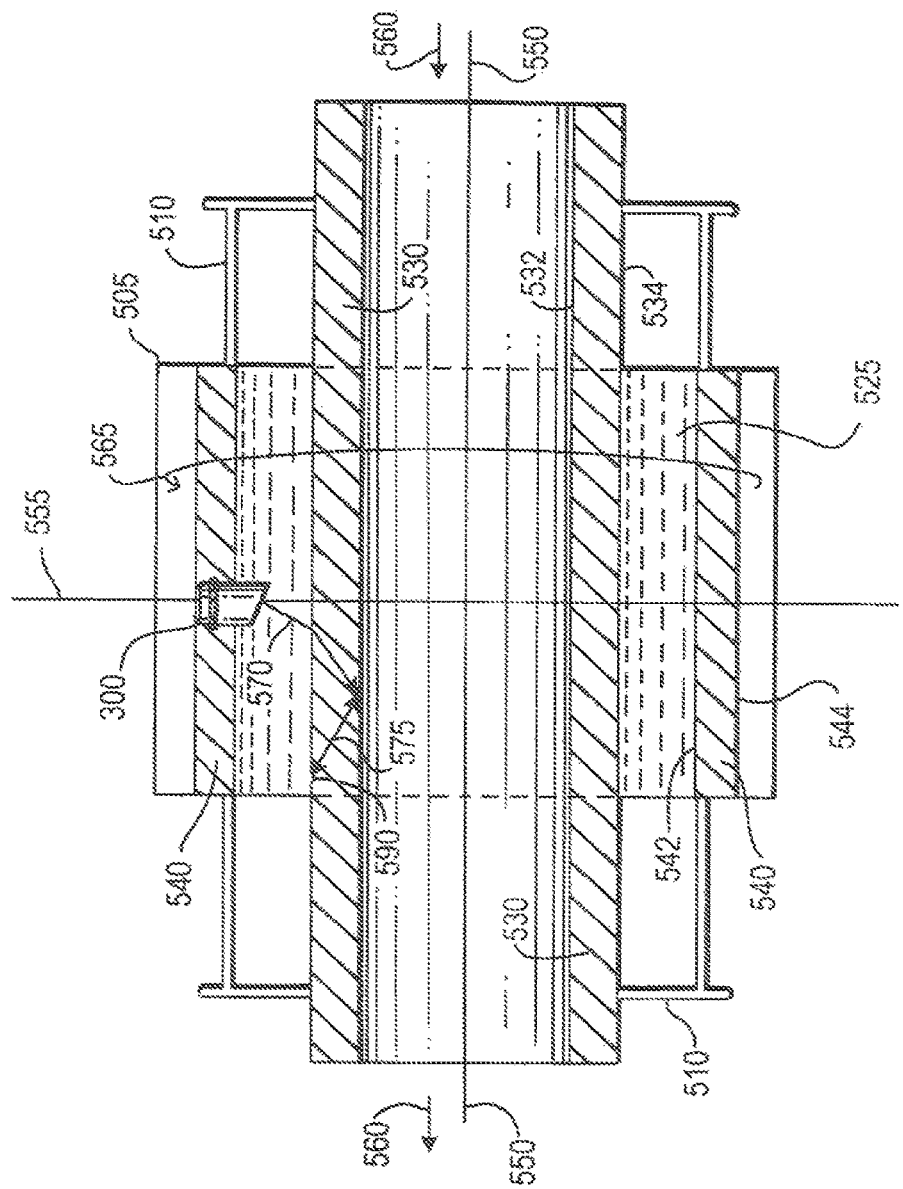
FIG. 7 is a cross-sectional view of the rotary tester and tube of FIG. 5, taken generally along the line 7-7, and showing the illustrative transducer of FIGS. 3-4 in accordance with certain embodiments of the present invention.

Because the angle of incidence is not 90 degrees, a portion of the incident beam 270 may be refracted at the interface between coupling medium 525 and outer surface 534 of tube 530. As illustrated, refracted beam 575 may bounce between inner surface 532 and outer surface 534 of tube 530, traveling in a direction that has two components: one component that is generally circular and that lies within the plane shown in FIG. 6 (i.e., the plane of tube 530's cross section), and one component that is generally along the length of tube 530 (i.e., within the plane containing radial axis 555 and longitudinal axis 550) as shown in FIG. 7. As a result, beam 575 may travel along a spiral path through tube 530, partly reflecting between inner surface 532 and outer surface 534, until beam 575 reaches a flaw 590 (which may be an oblique flaw). Beam 575 may then be reflected back from flaw 590 and refracted before reaching transducer 300 as beam 570.

The offset in direction 580 may be in either direction away from radial axis 555, provided the offset is contained within the same plane that is perpendicular to longitudinal axis 550 and that contains radial axis 555. These conditions hold as testing unit 540 and transducer 300 are rotated about longitudinal axis 550. The amount of the offset in direction 580 may depend on various factors such as the material being tested (the velocity of sound in the material of tube 530), the diameter of tube 530, etc.

As illustrated in FIG. 6, one component of the direction in which refracted beam 575 may travel may be a generally clockwise component that lies within the plane containing the cross section shown for tube 530. This component may be achieved by offsetting transducer 300 from axis 555 along direction 580. The magnitude of offset may be proportional to the diameter of tube 530 and may be reset for every diameter. As such, transducer 300 may be mounted on a rotatable disk (not shown) which may be affixed to testing unit 540 and adjusted to obtain the desired offset. To produce a refracted shear beam that travels in a direction having a counter-clockwise component, transducer 300 may simply be offset from axis 555, in the direction opposite to direction 580.

The other component of the direction in which refracted beam 575 may travel may be generally along the length of the tube and may be within the plane containing the tube's radial and longitudinal axes 555 and 550. The fact that the transducer is angled achieves this component. FIG. 7, which is a cross-sectional view of rotary tester 500 and tube 530 taken generally along line 7-7 of FIG. 5, shows testing transducer 300 emitting beam 570 in addition to being offset as shown in FIG. 6. Beam 570 is angled in a plane that is parallel to longitudinal axis 550. As discussed above, refracted beam 575 may travel through tube 530, partly reflecting between inner surface 532 and outer surface 534, until beam 575 reaches oblique flaw 590 and is reflected back and refracted before reaching transducer 300 as beam 570.

The component of the direction along which beam 575 is shown to be traveling in FIG. 7 is generally along direction 560. This may be referred to as forward-looking shear wave testing. Alternatively, transducer 300 may be rotated 180 degrees about radial axis 555 to produce beams that travel in the opposite direction for reverse-looking shear wave testing.

The foregoing describes a technique that can be used to detect oblique flaw 590 using a single transducer 300 that produces refracted beam 575 that may travel through tube 530 along a spiral path that has two components: one that is generally circular and one that lies within the plane of tube 530's cross section, and one that is generally along the length of tube 530. The resulting direction from summing these two components may be at a desired angle from each of the components. For example, the desired angle may be a 45-degree angle or any other angle(s).

Figure 8:
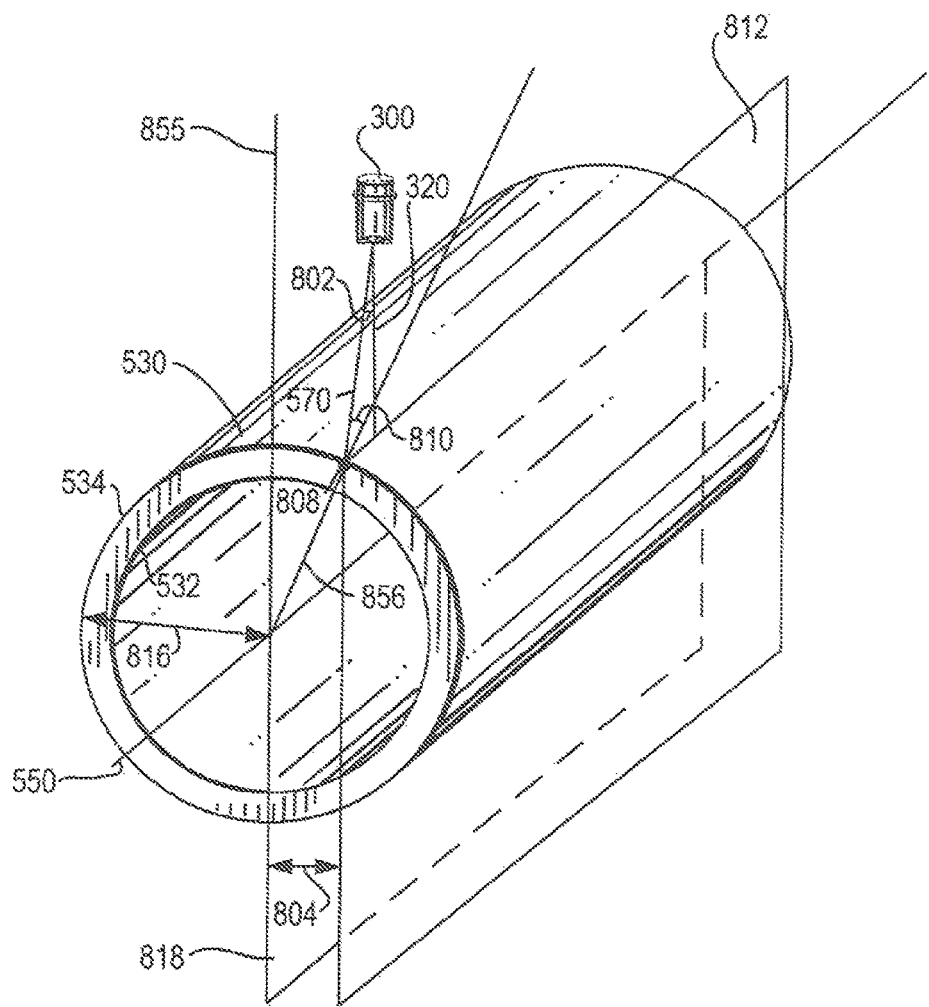
FIG. 8 is a perspective view of the tube of FIGS. 5-7 with the illustrative transducer of FIGS. 3-4 and 6-7 positioned for testing in accordance with certain embodiments of the present invention.

FIG. 8 is a perspective view of tube 530 of FIGS. 5-7 with transducer 300 of FIGS. 3-7 positioned for testing for oblique flaws according to the above discussion. Transducer 300 may be shaped so as to produce angled beam 570. Transducer 300 may also be offset in direction 580. However, the challenge lies in designating the appropriate incident angle that may be built into transducer 300 (which may be referred to as setting angle 802) and the amount by which transducer 300 may be offset (which may be referred to as offset 804) so as to effectively detect oblique flaws. The discussion below describes how setting angle 802 and offset 804 may be calculated.

In the configuration shown in FIG. 8, transducer 300 may be positioned so as to emit beam 570 which may enter tube 530 at point of general incidence 808. Radial axis 855 of tube 230 may be the radial axis along which a non-angled transducer would be positioned if it were to emit a beam perpendicular to outer surface 534 of tube 530 for longitudinal wave testing. Radial axis 855 and longitudinal axis 550 may be contained within plane 818. Transducer axis 320 and incident beam 570 may be contained in plane 812. Point of general incidence 808 may also be located on plane 812. Planes 812 and 818 may be parallel and the distance between them may correspond to offset 804. Setting angle 802 may correspond to the angle between incident beam 570 and transducer axis 320.

Radial axis 856 of tube 230, on the other hand, may be the radial axis which intersects outer surface 534 of tube 230 at point of general incidence 808. The angle of incidence (i.e., incident angle 810) may correspond to the angle between incident beam 570 and radial axis 856. The relationship between incident angle 810 and setting angle 802 may be geometrically calculated as follows:

$$SettinAngle802 = \arcsin\left(\sqrt{2} \sin\left(\frac{IncidentAngle810}{2}\right)\right)$$

Offset 804 may be proportional to the diameter of the tested object and may depend on the setting angle. More particularly, offset 804, which depends on external diameter 816 of tube 230 may be calculated as follows:

$$Offset804 = \frac{Diameter816}{2}\sin(SettingAngle802)$$

The above equations may be used to determine the setting angle for a transducer and the amount at which it may be offset based on a desired incident angle that may be best suited for testing for oblique flaws. The incident angle may be determined in accordance with Snell's law, which states that the ratio of the sine of the incident angle to the sine of the angle of refraction angle equals the ratio of the sound velocity in the medium of incidence to the sound velocity in the medium of refraction.

The ratio of the sound velocity in the medium of incidence to the sound velocity in the medium of refraction may be referred to as $\upsilon$ and the desired refraction angle may be referred to as $\alpha_r$. Accordingly, the equation set forth above for calculating the setting angle (which may be referred to as $\alpha_s$) may be rewritten as follows:

$$\alpha_s = \arcsin\left(\sqrt{2}\sin\left(\frac{\arcsin(\upsilon\sin\alpha_r)}{2}\right)\right)$$

When steel tubes are tested (i.e., the medium of refraction is steel) and water is used as coupling medium (i.e., the medium of incidence is water), the water-to-steel velocity ratio $\upsilon$ is approximately 0.4748. The refraction angle $\alpha_r$ is generally chosen to be 45 degrees so that substantial portions of the beam may be reflected back towards the transducer along the same path to ensure detectability. Plugging such values into the last equation set forth above yields a designated setting angle of approximately 13.5 degrees for detecting oblique flaws in steel tubes using an offset transducer immersed in water. The refraction angle $\alpha_r$ may vary within +/−5 degrees to maintain reliable detectability. Alternatively, any other refraction angle in reference to the cross section of the tube may be chosen. Similarly, the setting angle $\alpha_s$ may vary by +/−2 degrees and may be different from the angle used for transverse flaw detection in which the transducer is not horizontally offset.

Thus, once the coupling medium and tested material are chosen, choosing an appropriate setting angle that may be built into the transducer (or at which a-regular transducer—i.e., one that does not have an emission angle built in—may be tilted) to detect oblique flaws may merely depend on the desired refraction angle in the object to be tested.

Referring to the external diameter of the tested object as D, the equation set forth above for calculating the offset, which may also be referred to as A, may be rewritten as follows:

$$A = \frac{D}{2}\sin(\alpha_s)$$

Referring back to FIGS. 5-8, transducer 300 may be mounted so as to perform shear wave testing. While tube 530 is moved in direction 560, the transducer may rotate about longitudinal axis 550 in direction 565 during testing. This combination of motions results in helical test traces around the circumference of tube 530. These traces slightly overlap to ensure reliable flaw detection and achieve 100 percent inspection. Additional transducers may also be used for longitudinal wave testing, thickness measurements, transverse flaw detection, longitudinal flaw detection, etc.

Several transducers 300 may be used in rotary tester 500 to detect the largest range of orientation of angles possible for oblique flaws in addition to a basic setup that utilizes five transducers for performing clockwise and counter-clockwise longitudinal, forward and reverse transverse flaw detection and a wall thickness measurement. For example, a first transducer 300, may be used for performing clockwise, forward-looking shear wave testing. A second may be used for performing counter-clockwise, forward-looking shear wave testing. A third may be used for performing clockwise, reverse-looking shear wave testing. A fourth may be used for performing counter-clockwise, reverse-looking shear wave testing. Moreover, in case it is required to cover the range of 25-to-45 degrees of directions, an additional transducer may be assigned to each five degrees of increments.

Several problems may be nevertheless associated with increasing the number of transducers used. Because each transducer may require a separate channel, the number of channels used for analyzing the signals emitted and received from transducers would increase. Accordingly, the number of required coupling capacitors would also increase. In turn, this would complicate the required rotary connections. However, rotary testers have a limited number of testing channels available and large number of channels require longer changeover time from one size of tube to another. Although the signals received from individual transducers may be multiplexed to decrease the number of channels, the inspection speed may significantly diminish in order to preserve reliability. Furthermore, the mounting space on the rotor may be limited and transducer cross-talk can become a greater problem.

Fortunately, cracks in pipes and tubes are more likely to occur in specific directions depending on the manufacturing process. These directions and corresponding angles can be identified during production. For example, if a diagonal rolling motion is encountered, the orientation of defects may be determined by the rolling direction. Manufacturers may therefore specify direction and angle requirements for detecting oblique flaws, and a reduced number of transducers may be used to fit such requirements. For example, with respect to a requirement for oblique detection capability adjustable to 35+/−10 degrees in two directions, two transducers 300 may be used so long as one performs clockwise shear wave testing, and the other, counter-clockwise shear wave testing. In such a case, the number of testing transducers, hence the number of channels, required for reliable longitudinal, transverse and oblique flaw detection can be limited to six, with only two of them being transducers that are dedicated to detect oblique flaws oriented in different directions, such as transducer 300.

Therefore, reliable oblique flaw detection may be achieved without reducing inspection speed, significantly adding to transducer cross-talk, or requiring significant electronic hardware or processing additions such as multiple transducers, coupling capacitors, connections and testing channels. Moreover, no additional mounting hardware would be required because the transducers that are designed for oblique flaw detection may have the designated angle built into their housing as shown in FIGS. 3 and 4. Alternatively, a regular transducer may also be used to detect oblique flaws if additional hardware is available to tilt the transducer so as to emit the desired angled beam. For higher inspection speeds or thickness measurements, additional hardware and processing may be required.

Thus it is seen that systems and methods for horizontally offsetting a small number of angled transducers that each use pulse-echo testing to generate shear waves for detecting oblique surface and internal flaws have been provided.

One of ordinary skill in the art should appreciate that the present invention may be practiced in embodiments other than those described herein. For example, angled and offset transducers may be used in a testing apparatus other than a rotary tester. Moreover, the transducers described above may be used to test a flat object, such as a plate, without moving about its surface.

It will be understood that the foregoing is only illustrative of the principles of the present invention, and that various modifications can be made by those skilled in the art without departing from the scope and spirit of the invention, and the invention is limited only by the claims that follow.

What is claimed is:
1. A method, comprising:
causing a transducer to emit a beam that is focused at a point and emitted toward a surface of an object, wherein the emitted beam contacts the surface at oblique angles, such that a refracted beam travels through a portion of the object along multiple directions when the transducer emits the beam.

2. The method of claim 1, wherein the beam is a cylindrically focused beam having a focal length substantially equal to a diameter of the object.

3. The method of claim 1, wherein a position of the transducer is at an offset and an angle relative to the object, and the position causes the emitted beam to contact the surface at the oblique angles.

4. The method of claim 3, wherein the offset is based at least in part on the angle.

5. The method of claim 3, wherein the offset is based at least in part on a diameter of the object.

6. The method of claim 3, wherein the offset is in a direction perpendicular to a radial axis of the object.

7. The method of claim 3, wherein the angle is in a first plane parallel to a second plane defined by the longitudinal axis of the object and a radial axis of the object.

8. The method of claim 3, wherein the multiple directions include a first direction that is substantially cyclical and lies within a plane of a cross section of the object and a second direction that is substantially parallel to the longitudinal axis of the object.

9. The method of claim 1, further comprising determining whether a flaw exists in the object.

10. The method of claim 9, further comprising receiving a reflected signal caused by a partial reflection of the refracted beam in the object, wherein determining whether a flaw exists in the object comprises comparing the emitted beam with the reflected signal.

11. A system, comprising:
a transducer configured to emit a beam toward a surface of an object, wherein:
the beam is focused at a point, and
the emitted beam contacts the surface at oblique angles, such that a refracted beam travels through a portion of the object along multiple directions when the transducer emits the beam.

12. The system of claim 11, wherein the beam is a cylindrically focused beam having a focal length substantially equal to a diameter of the object.

13. The system of claim 11, wherein a position of the transducer is at an offset and an angle relative to the object, and the position causes the emitted beam to contact the surface at the oblique angles.

14. The system of claim 13, wherein the offset is based at least in part on the angle.

15. The system of claim 13, wherein the offset is based at least in part on a diameter of the object.

16. The system of claim 13, wherein the offset is in a direction perpendicular to a radial axis of the object.

17. The system of claim 13, wherein the angle is in a first plane parallel to a second plane defined by the longitudinal axis of the object and a radial axis of the object.

18. The system of claim 13, wherein the multiple directions include a first direction that is substantially cyclical and lies within a plane of a cross section of the object and a second direction that is substantially parallel to the longitudinal axis of the object.

19. The system of claim 11 further comprising a flaw detector configured to determine whether a flaw exists in the object.

20. The system of claim 19, wherein the flaw detector determines whether a flaw exists in the object by comparing the emitted beam with a reflected signal caused by a partial reflection of the refracted beam in the object.

* * * * *